(12) United States Patent
Martin et al.

(10) Patent No.: US 8,518,020 B2
(45) Date of Patent: Aug. 27, 2013

(54) SAFETY URINARY CATHETER

(75) Inventors: George L. Martin, Scottsdale, AZ (US); David M. Mumma, Phoenix, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 41 days.

(21) Appl. No.: 13/214,599

(22) Filed: Aug. 22, 2011

(65) Prior Publication Data

US 2012/0078235 A1   Mar. 29, 2012

Related U.S. Application Data

(60) Provisional application No. 61/376,094, filed on Aug. 23, 2010.

(51) Int. Cl.
*A61M 37/00* (2006.01)

(52) U.S. Cl.
USPC ............... 604/544; 604/8; 128/349; 128/246

(58) Field of Classification Search
USPC ........................................ 604/544; 606/153
See application file for complete search history.

(56) References Cited

U.S. PATENT DOCUMENTS

| 3,543,759 | A |   | 12/1970 | McWhorter |
|---|---|---|---|---|
| 3,593,713 | A | * | 7/1971 | Bogoff et al. ............ 604/102.02 |
| 3,924,634 | A | * | 12/1975 | Taylor et al. ............ 604/100.01 |
| 5,007,919 | A | * | 4/1991 | Silva et al. .................... 606/194 |
| 5,052,998 | A | * | 10/1991 | Zimmon ........................... 604/8 |
| 5,919,170 | A |   | 7/1999 | Woessner |
| 2006/0025753 | A1 |   | 2/2006 | Kubalak et al. |
| 2006/0135951 | A1 |   | 6/2006 | Meek et al. |
| 2009/0030370 | A1 |   | 1/2009 | Nishtala et al. |
| 2009/0299261 | A1 |   | 12/2009 | Bognar |
| 2010/0145315 | A1 |   | 6/2010 | House |

FOREIGN PATENT DOCUMENTS

WO   WO2009012336 A1   1/2009

* cited by examiner

*Primary Examiner* — Leslie Deak
*Assistant Examiner* — Jordan B Bailey
(74) *Attorney, Agent, or Firm* — Fish & Richardson P.C.

(57) ABSTRACT

This document provides catheters (e.g., urinary catheters) having safety mechanisms that indicate when a distal end of the device enters an intended cavity (e.g., a human's bladder) and is properly positioned, thereby preventing inflation of a retention balloon in an unintended location (e.g., the urinary canal). For example, safety urinary catheters and methods for using and inserting such safety urinary catheters are provided.

31 Claims, 9 Drawing Sheets

SAFETY URINARY CATHETER

CROSS-REFERENCE TO RELATED APPLICATION

This application claims the benefit of U.S. Provisional Application No. 61/376,094, filed Aug. 23, 2010. The contents of the foregoing application is hereby incorporated by reference in their entireties.

BACKGROUND

1. Technical Field

This document relates to urinary catheters with a safety mechanism that indicates when the distal end of the device entered a human's bladder and is properly positioned, thereby preventing inflation of the retention balloon in the urinary canal. For example, this document provides urinary catheters that can include a body having a proximal portion and a distal portion with the body having a safety mechanism to indicate when the distal portion of the catheter body has entered the urinary bladder.

2. Background Information

Catheters are medical devices that can be used to facilitate various medical procedures. A catheter can be inserted into the body of a patient and thereby allow drainage or removal of fluids or other material. For instance, a typical internal urinary catheter is known as a Foley catheter. A Foley catheter can include a hollow tube having a tip at one end which is inserted into the body. The tip can have one or more openings that communicate with the interior of the hollow tube. The other end of the tube can be disposed externally of the body and can be connected to a waste receptacle by way of a flexible discharge conduit. An annular inflatable portion, or retention balloon, can be spaced inwardly from the tip. Such a balloon can be deflated during placement of the catheter into the body and thereafter inflated after the tip is properly positioned within the body in the urinary bladder of the patient.

SUMMARY

This document provides catheters having a safety mechanism that is capable of indicating when the distal end of the device entered a bladder (e.g., a human's bladder) and is properly positioned, thereby preventing inflation of a retention balloon in the urinary canal. In some cases, a urinary catheter can be improperly inserted so that inflation of the retention balloon is initiated while it is still within the urethra (urinary canal). The force exerted by the retention balloon on the walls of a restricted body channel may cause disastrous complications such as ruptured channel walls in addition to considerable patient discomfort. A urinary catheter provided herein can be used to avoid such improper insertions and such complications.

As described herein, a catheter can be designed to have a body having a proximal portion and a distal portion, a retention balloon near the end of the distal portion, and a safety element on the catheter body located proximal to the retention balloon. The catheter can be configured such that the safety element changes position when the retention balloon is inside a body cavity. The catheter can be a urinary catheter. The catheter can be a Foley catheter.

In some cases, the safety element can be a flexible flap. The safety element can be attached to the catheter body immediately proximal to the retention balloon. The safety element can be made out of the same material as the catheter body or a different material. The safety element can be folded against the catheter body while the catheter is within a body passage, urinary canal, or urethra. The safety element can become extended when it is inside a body cavity such as the urinary bladder. The safety element can be perpendicular to the longitudinal axis of the catheter body. The safety element can be connected to a communication structure near the distal tip of the safety element.

A communication structure can be connected to the distal tip of the safety element by being securely tied to the distal tip or by being molded into the safety element. The communication structure can enter the catheter body through an opening that is proximal to the connection point of the safety element. The opening can connect to the drainage lumen. The opening can connect to a communication structure lumen that is specific for the communication structure. In some cases, the communication structure can be located outside the catheter body. The communication structure can be a long piece of suture that extends the length of the catheter. In some cases, a communication structure can be a latex band.

A communication structure can be designed to have an indicator near the proximal end. Such an indicator can be a specific length of the communication structure that is a color or pattern that contrasts the other portions of the communication structure. In some cases, the indicator can be a knot or a bead. The indicator can change position along the longitudinal axis depending upon the configuration of the safety element. When the safety element is in a folded configuration, the indicator can be in a more proximal position. In the more proximal position, the indicator can be located distal to the funnel. When the safety element is in an extended configuration and perpendicular or nearly perpendicular to the longitudinal axis, the indicator can be in a more distal position. In the more distal position, the indicator can be located inside the funnel. In the more distal position, the indicator can be flush with the proximal end of the funnel. In the more distal position, the indicator can be distal to the funnel. The position of the indicator can indicate whether or not the retention balloon can be inflated. If the indicator is in the more proximal position, the retention balloon should not be inflated. If the indicator is in the more distal position, the retention balloon can be inflated.

This document also provides methods for using a catheter with a safety mechanism to know when the distal end of the catheter has entered a human's body cavity. In some cases, a method provided herein can include applying lubrication to at least a portion of the catheter. The lubricant can include a water-based lubricant. The catheter can be a Foley catheter, and the body cavity can be the urinary bladder. The method can include attaching a pump to the inflation lumen of the catheter and a tube that connects to a urine storage bag to the drainage lumen of the catheter. This step may optionally be performed later in the method. The method can include using an introducer tip that defines an insertion opening. The introducer tip can be used to insert the distal end of the catheter body in a bodily opening and into a human's bodily passage. The bodily opening can be the meatus, and the bodily passage can be the urinary canal or the urethra. The method can include advancing the catheter into the bodily passage while monitoring the distal portion of the safety mechanism that has a visible indicator that is distal to the funnel. The method can include stopping the advancement of the catheter when the position of the indicator changes in relationship to the funnel along the longitudinal axis of the catheter body. The indicator may no longer be visible once the displacement in the longitudinal direction has occurred. The change in location of the indicator along the longitudinal axis from a more proximal position to a more distal position can indicate that the retention balloon has entered a body cavity. The body cavity can be a urinary bladder. The method can include inflating the retention balloon after the change in the position of the indicator has been observed. The method can include using the catheter with a safety mechanism to enable a human to void his or her bladder.

In general, one aspect of this document features a catheter comprising, or consisting essentially of, (a) a body having a proximal portion and a distal portion, (b) a retention balloon near the end of the distal portion, and (c) a safety element on the body located proximal to the retention balloon, wherein the catheter is configured such that the safety element changes position when the retention balloon is inside a body cavity. The safety element can comprise a flap located proximal to the retention balloon and can be connected to a communication structure. The flap can be folded against the catheter while the catheter is inserted, and the flap can be extended only when the retention balloon is inside the body cavity. The communication structure can be a suture that extends from the tip of the safety element to the proximal end of the catheter. The communication structure can comprise an indicator that signals when the safety element is extended or non-extended. The flap can be latex. The catheter can be a urinary catheter. The catheter can be a Foley catheter. The body cavity can be a urinary bladder.

In another aspect, this document features a method for using a catheter comprising, or consisting essentially of, (a) inserting a catheter into a patient, the catheter comprising, or consisting essentially of, a body having a proximal portion and a distal portion, a retention balloon near the end of the distal portion, a safety mechanism on the body located proximal to the retention balloon, and (b) inflating the retention balloon after the safety mechanism signals when the retention balloon is inside a body cavity.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
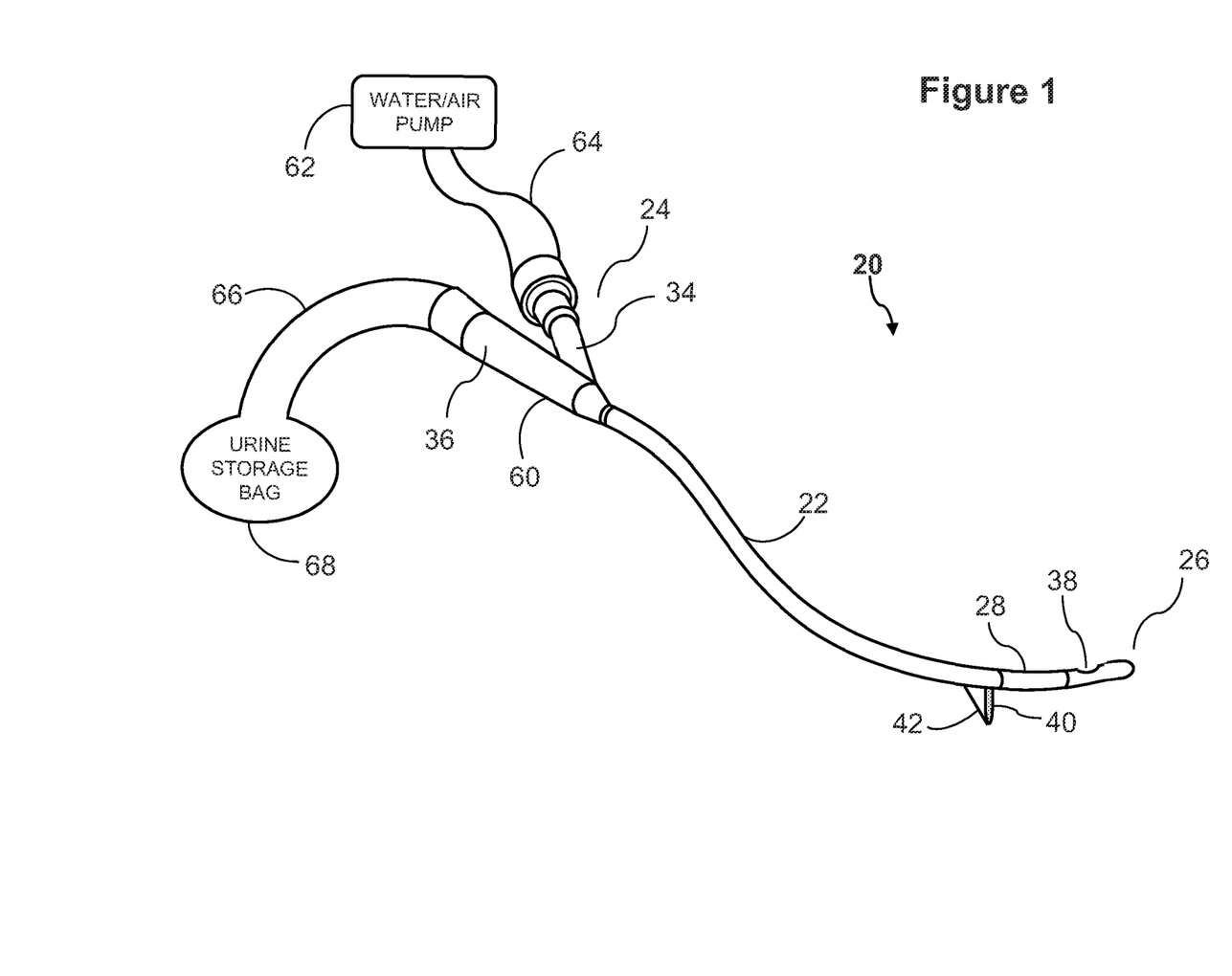
FIG. 1 is a perspective view of a catheter in accordance with one embodiment.

FIG. 1 is a perspective view of a Foley-type catheter generally designated with reference number 20. Catheter 20 can be made of polyvinyl chloride (PVC), polyurethane, silicone rubber, nitrile rubber, or other appropriate material that is biocompatible, hydrophobic, and generally inert with respect to physiological fluids it contacts. Catheter 20 can have a polished surface. Catheter 20 (e.g., urinary catheter) can be between fifteen and fifty-five centimeters in length and between fifteen and seventy millimeters in diameter.

To assist in the description of the components of catheter 20, the following coordinate terms are used. A "longitudinal axis" is generally parallel to a section of the catheter. In FIG. 1, the longitudinal axis is generally parallel to an elongated flexible body portion 22. As used herein, "the longitudinal direction" refers to a direction substantially parallel to the longitudinal axis. The term "distal" is used in reference to an end of catheter 20 near the patient's body. The term "proximal" is used in reference to an end of catheter 20 near a funnel 60.

Catheter 20 can include a catheter body 22 with a proximal end 24 and a distal end 26. Catheter 20 can include a funnel 60 at or near proximal end 24. Funnel 60 can define one or more lumens. For example, funnel 60 can be split to define an inflation lumen 34 and a drainage lumen 36. Inflation lumen 34 can extend to a water/air pump 62 through a tube 64. Water/air pump 62 can be employed to flow water or air into inflation lumen 34. Drainage lumen 36 can extend to a urine storage bag 68 through a tube 66. Urine storage bag 68 can be employed to collect discharged urine from a patient.

Figure 2A:
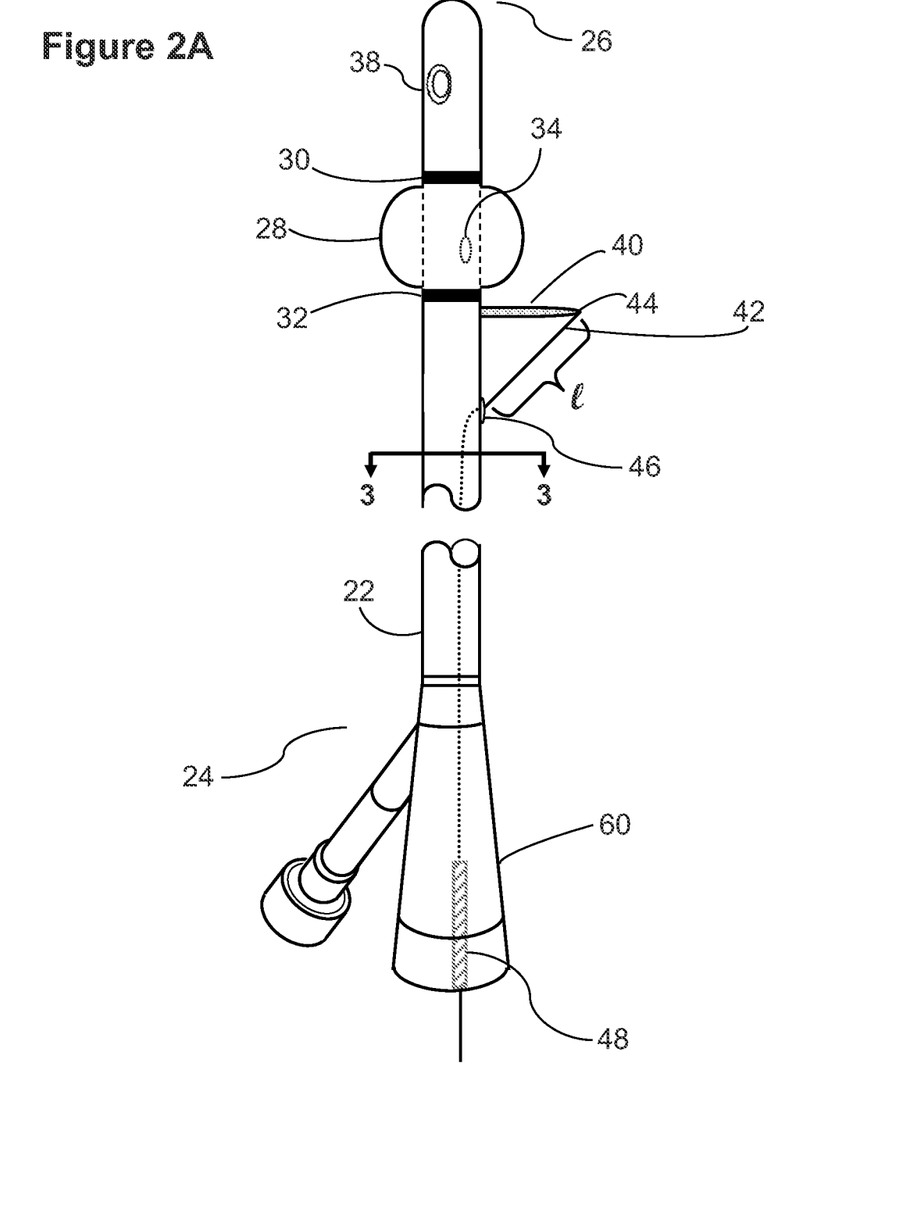
FIG. 2A is a close up view of proximal and distal ends of a catheter when a safety element is in an extended configuration in accordance with one embodiment.
Figure 2B:
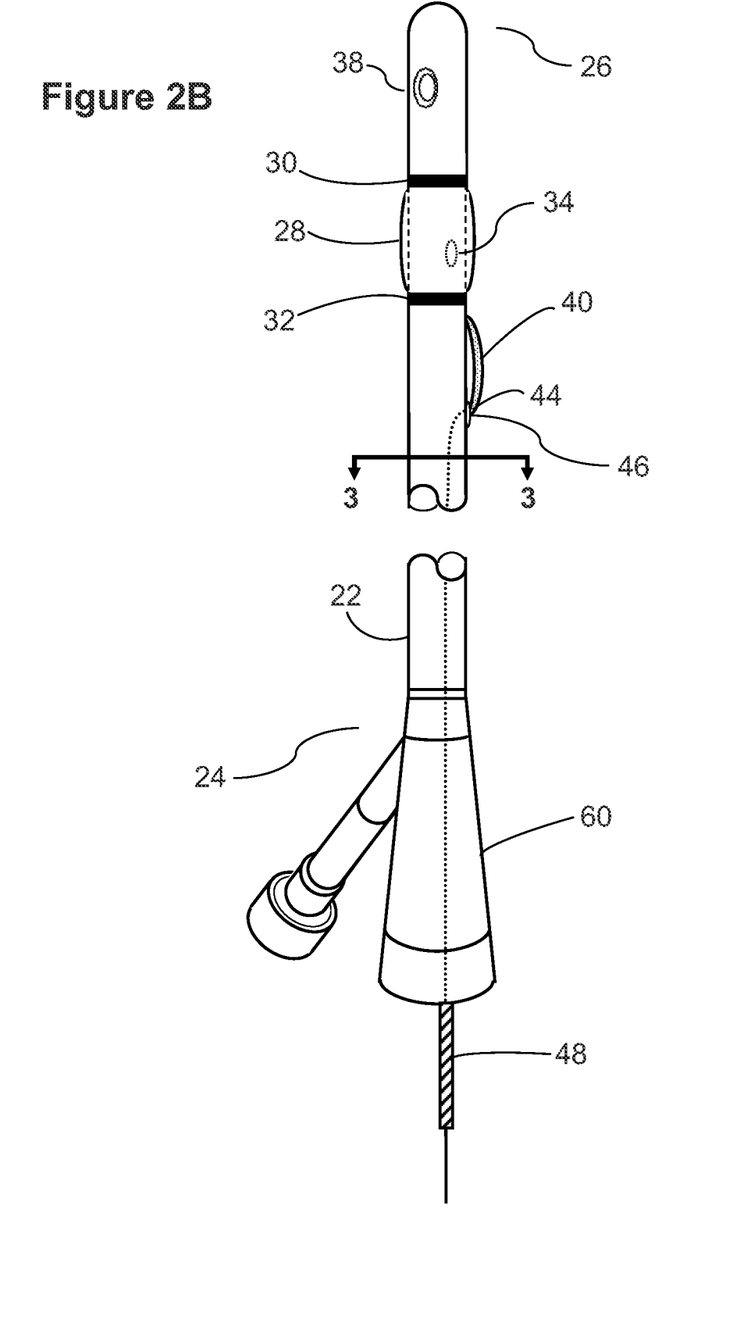
FIG. 2B is a close up view of proximal and distal ends of a catheter when a safety element is in a folded configuration in accordance with one embodiment.

Catheter 20 can include a retention balloon 28. With reference to FIGS. 2A and 2B, catheter 20 can include fluid tight seals 30 and 32. Retention balloon 28 can be deflated for insertion into a patient. Pump 62 can pump water through inflation lumen 34 and ultimately into retention balloon 28 located in the patient's bladder. Retention balloon 28 can retain distal end 26 of catheter 20 in the bladder, and maintain a drainage port 38 in the proper position to allow urine to pass through.

Drainage lumen 36 can extend from distal end 26 to proximal end 24. At proximal end 24, fluid (e.g., urine) passing through drainage lumen 36 can enter funnel 60 and continue to pass through tube 66 to urine storage bag 68. While funnel 60 may be connected to urine storage bag 68 for an extended period of time, it may only need to be connected to water/air pump 62 for a long enough period of time to inflate retention balloon 28 of catheter 20.

Distal end 26 can include one or more openings 38 in fluid communication with drainage lumen 36 to facilitate drainage of urine from a bladder of a patient. In one embodiment, catheter 20 can have one opening 38 at distal end 26. Any number of openings can be used. For example, distal end 26 can have one, two, three, four, five, or more openings. The opening 38 shown is oval shaped. Opening 38 can be any appropriate shape, such as circular or rectangular. If multiple openings are present, each opening can be configured to have the same shape or a different shape. In some cases, if multiple openings are present, the multiple openings can be positioned in a variety of ways. For example, the openings can be positioned along the same longitudinal line. In some cases, the openings can be positioned equidistant from distal end 26 of catheter 20. The openings can be positioned according to any combination of spacing about the outer surface of catheter 20 at distance from the tip of catheter 20.

FIGS. 2A and 2B are close-up views of distal end 26 and proximal end 24 of catheter 20. A catheter provided herein can include a safety mechanism. A safety mechanism can include a safety element 40 connected to a communication structure 42. Safety element 40 can be connected to catheter body 22 proximal to retention balloon 28. In one embodiment, safety element 40 can be a flexible flap that is connected to catheter body 22 proximal to retention balloon 28.

Safety element 40 can be made out of polyvinyl chloride (PVC), silicone rubber, nitrile rubber, latex, or other appropriate material. For example, safety element 40 can be a flap made out of the same material as catheter 20 or a different material. Safety element 40 can be permanently affixed to catheter body 22 or detachable. If safety element 40 is detachable, it can be removed from catheter 20 by pulling firmly on communication structure 42 at proximal end 24 of catheter 20. In some case, a catheter provided herein can be designed to have a safety element 40 that is not a balloon and is not inflatable. In some cases, a catheter provided herein can be designed to have a safety element 40 that is non-inflatable.

Safety element 40 can be connected to catheter body 22 in such a way that when safety element 40 is in an extended configuration, it is about perpendicular to the longitudinal axis, as shown in FIG. 2A. FIG. 2B shows a folded or bent position of safety element 40. This folded or bent position can be used when catheter 20 has not yet reached the bladder. When catheter 20 is inserted and advanced into the urinary canal, safety element 40 is flexible enough so it folds against catheter body 22 such that safety element 40 is parallel or almost parallel with the longitudinal axis. Safety element 40 can have enough flexibility so that it can extend away from catheter body 22 when not restrained or restricted by, for example, a urinary canal. Safety element 40 can be between 5 mm and 30 mm in length.

Communication structure 42 can be attached to a distal tip 44 of safety element 40. In some cases, communication structure 42 can extend in the longitudinal direction and can be visible at a proximal end 24 of catheter 20. In some cases, communication structure 42 can be securely tied to distal tip 44 of safety element 40 or molded into safety element 40. With further reference to FIGS. 2A and 2B, communication structure 42 can enter catheter body 22 at an opening 46 that can be proximal to a point where safety element 40 is connected to catheter body 22. FIG. 2A shows safety element 40 in an extended configuration, with communication structure 42 connected to distal tip 44 of safety element 40 such that length l of communication structure 42 is pulled outside catheter body 22. The proximal end of communication structure 42 can be placed into urine storage bag 68 or it can be excluded from urine storage bag 68 when urine storage bag 68 is attached to tube 66 by compressing communication structure 42 in a seal. In some cases, there can be a small hole in the proximal end of catheter body 22 for communication structure 42 to exit an internal portion of catheter 20 such that communication structure 42 does not come into contact with drainage lumen 36, tube 66, or urine storage bag 68.

In one embodiment, communication structure 42 can be a suture. In some cases, communication structure 42 can be a string, ribbon, or latex band.

When safety element 40 is folded against catheter body 22, an indicator 48 on communication structure 42 can be seen at proximal end 24 near a base of funnel 60. FIG. 2B shows an indicator 48 that is visible at proximal end 24 near the base of funnel 60. When indicator 48 on communication structure 42 is visible, it signals that safety element 40 is in the folded configuration and retention balloon 28 should not be inflated.

FIG. 2A shows safety element 40 in an extended configuration, and indicator 28 is no longer visible outside funnel 60. When safety element 40 has been advanced completely into the urinary bladder, safety element 40 can become perpendicular to the longitudinal axis, causing communication structure 42 to be pulled towards distal end 26 and indicator 48 to no longer be visible at proximal end 24 of catheter 20.

Indicator 48 of communication structure 42 can be a different color or pattern than the rest of communication structure 42. For example, indicator 48 can be red. Indicator 48 can be a segment on communication structure 42 that is the same length as l (FIG. 2A) that is displaced when safety element 40 moves from a folded configuration to an extended configuration. In some cases, indicator 48 can be a knot or a bead. Indicator 48 can be a different type of material than the other portions of communication structure 42. For example, indicator 48 can be a suture, and communication structure 42 can be latex or vice-versa. Indicator 48 can be located at a position on communication structure 42 such that indicator 48 is visible when safety element 40 is in a folded configuration and not visible when safety element 40 is in an extended configuration.

Figure 3A:
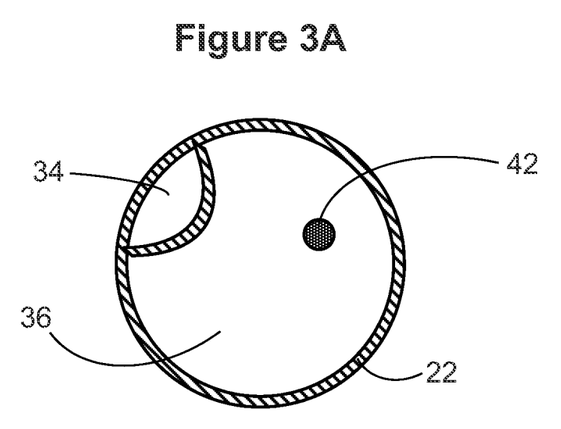
FIGS. 3A and 3B are cross sectional views taken along line 3-3 of FIGS. 2A and 2B, in accordance with some embodiments.
Figure 3B:
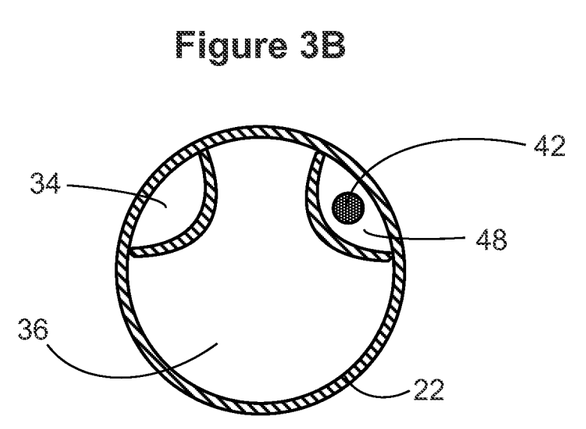

FIGS. 3A and 3B are cross sectional views taken along line 3-3 in FIGS. 2A and 2B. With reference to FIG. 3A, openings 38 and 46 shown in FIGS. 2A and 2B can be connected to drainage lumen 36, and communication structure 42 can be configured to extend within drainage lumen 36. In some alternative embodiments, with reference to FIG. 3B, opening 46 shown in FIGS. 2A and 2B can be connected to a communication structure lumen 48, which is a separate lumen specifically for communication structure 42 to pass through to proximal end 24 of catheter 20. In either drainage lumen 36 or communication structure lumen 48, there may be a hook or loop (not shown) at proximal end 24 to hold communication structure 42 to one side of funnel 60.

Figure 4A:
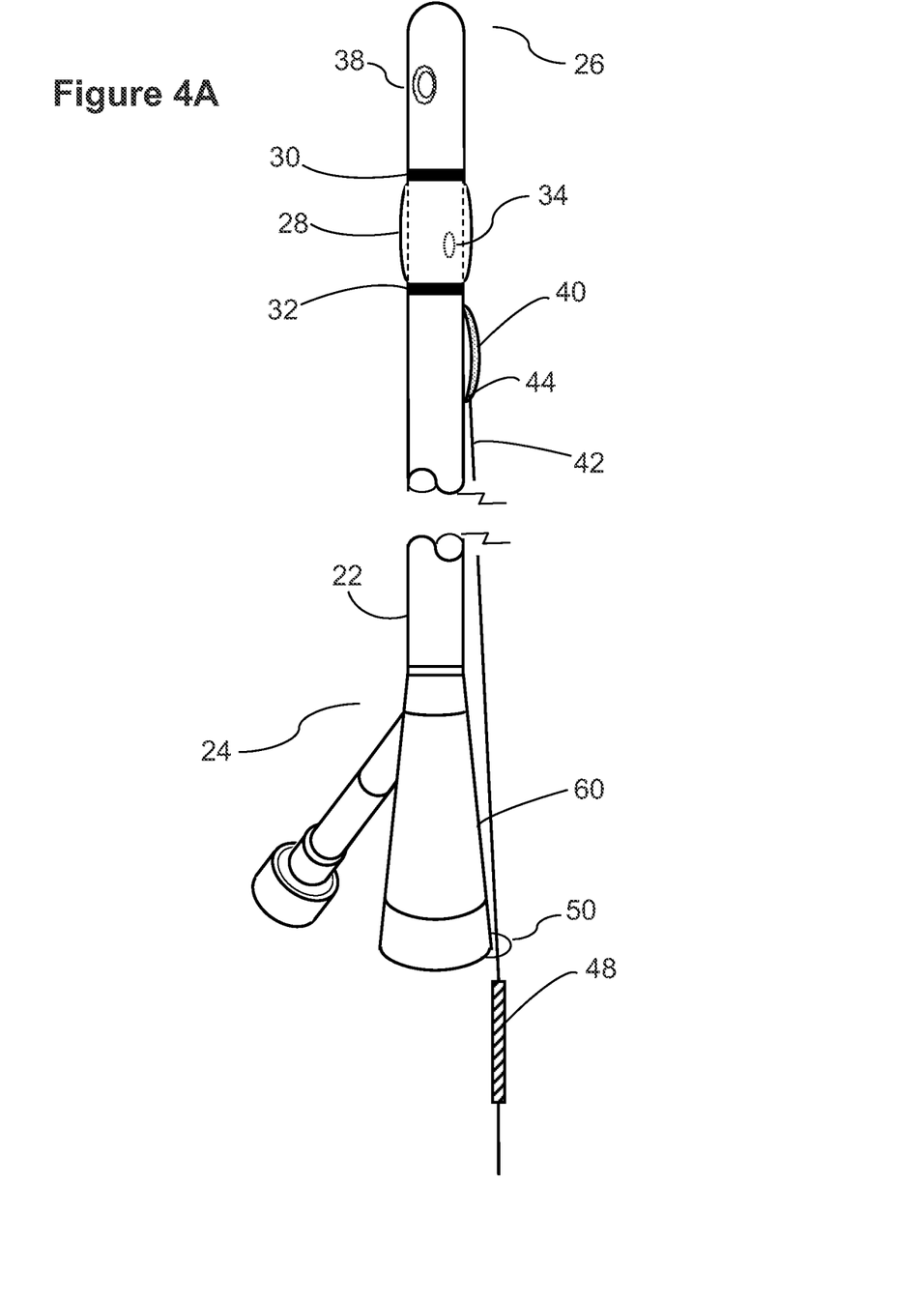
FIG. 4A is a close up view of proximal and distal ends of a catheter when a safety element is in a folded configuration in accordance with one embodiment.
Figure 4B:
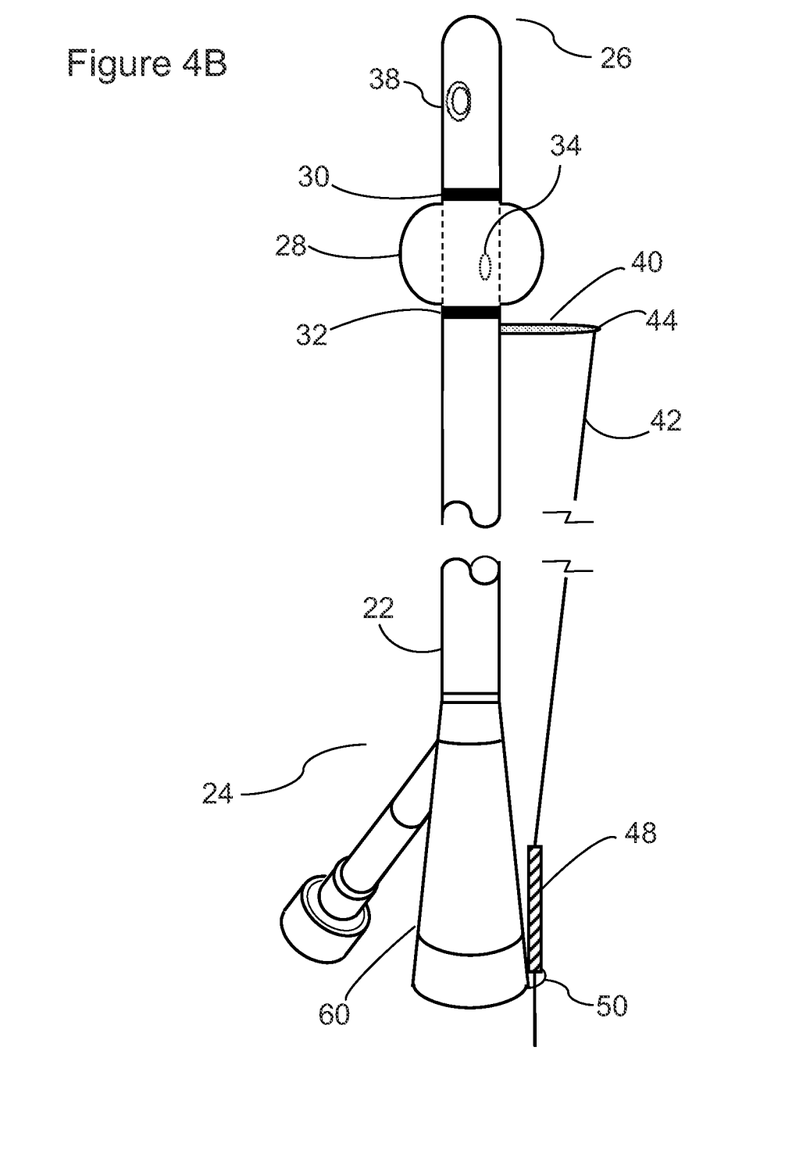
FIG. 4B is a close up view of proximal and distal ends of the catheter of FIG. 4A when the safety element is in an extended configuration in accordance with one embodiment.

FIGS. 4A and 4B are close-up views of distal end 26 and proximal end 24 of catheter 20 with an alternative embodiment of a safety mechanism. In such cases, a safety mechanism can included a safety element 40 that is proximal to a retention balloon 28. Communication structure 42 can be connected to a distal tip 44 of safety element 40 but does not enter catheter 20 through an opening. Communication structure 42 can run parallel to catheter body 22 along the longitudinal axis to proximal end 24 of catheter 20. There can optionally be a hook or a loop 50 on or near funnel 60 to hold communication structure 42 in close proximity to proximal end 24 of catheter 20. Communication structure 42 can optionally be enclosed within a lumen that is connected to but is external to catheter body 22 as opposed to internal (lumen not shown). In FIG. 4A, safety element 40 is folded against catheter body 22, and an indicator 48 on communication structure 42 is visible past funnel 60 at proximal end 24 of catheter 20. When indicator 48 on communication structure 42 is located proximally to funnel 60, it signals that safety element 40 is still within the urinary canal and that retention balloon 28 should not be inflated. When safety element 40 has been advanced completely into the urinary bladder, safety element 40 becomes perpendicular to the longitudinal axis, causing communication structure 42 to be pulled towards distal end 26 and indicator 48 to be displaced along the longitudinal axis of catheter body 22. In this embodiment, indicator 48 can always be visible and the position of indicator 48 can signal the configuration of safety element 40. FIG. 4B shows safety element 40 in an extended configuration that would occur when it is inside the bladder. Indicator 48 is now located just above the proximal end of funnel 60. When indicator 48 has shifted distally from its original position, this signals that retention balloon 28 can be inflated. Safety element 40 can optionally be detachable from catheter body 22. Safety element 40 can be removed from catheter 20 by pulling firmly on communication structure 42 at proximal end 24 of catheter 20.

The embodiments shown in FIGS. 4A-4B where communication structure 42 is not housed within drainage lumen 36 may help to reduce the risk of an infection. Additionally, catheter 20 can be configured so communication structure 42 never comes into contact with drainage lumen 36, tube 66, or urine storage bag 68 which may also reduce infection risk.

Figure 5A:
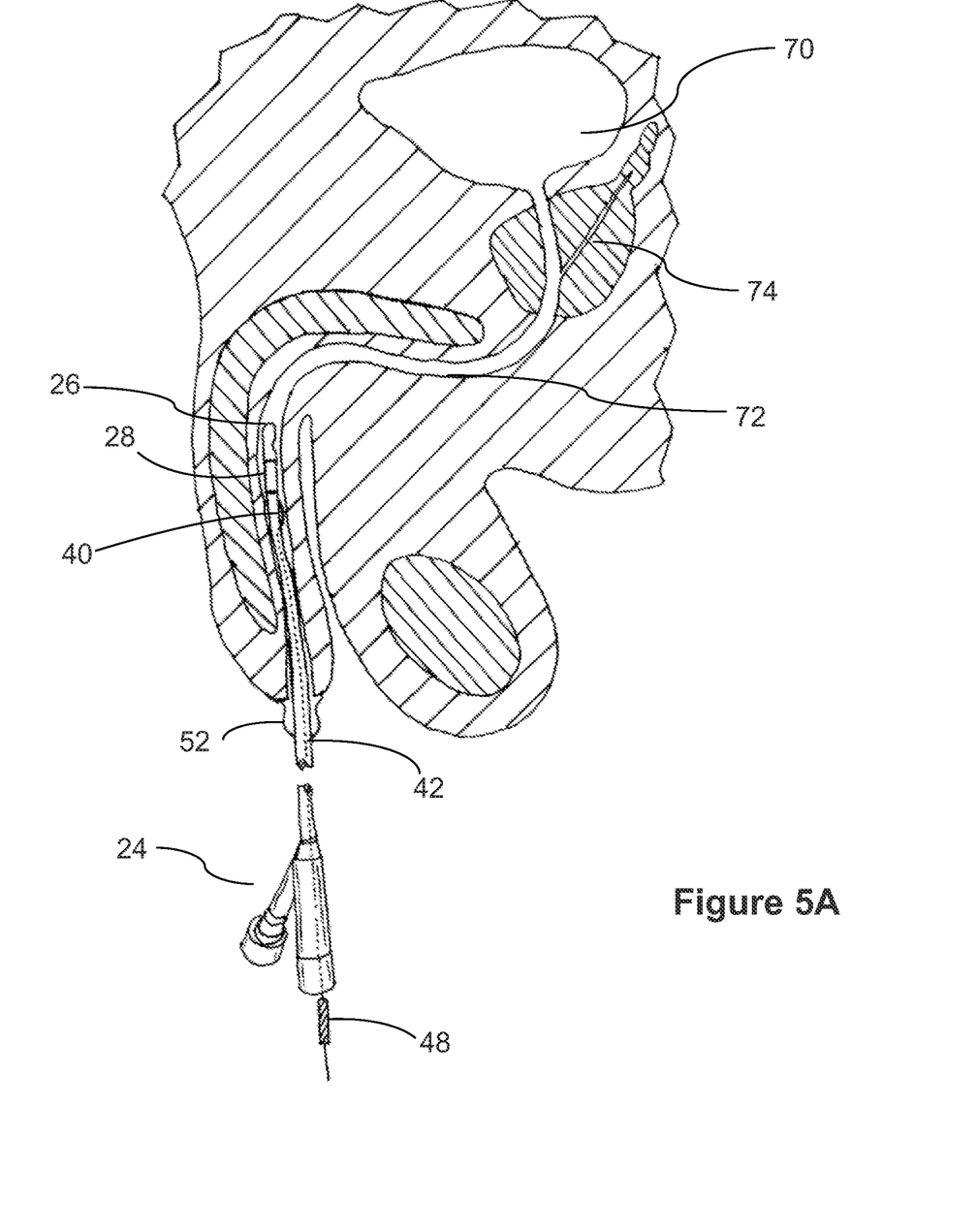
FIG. 5A is a side view of the urinary catheter during insertion into a urinary canal in accordance with one embodiment.
Figure 5B:
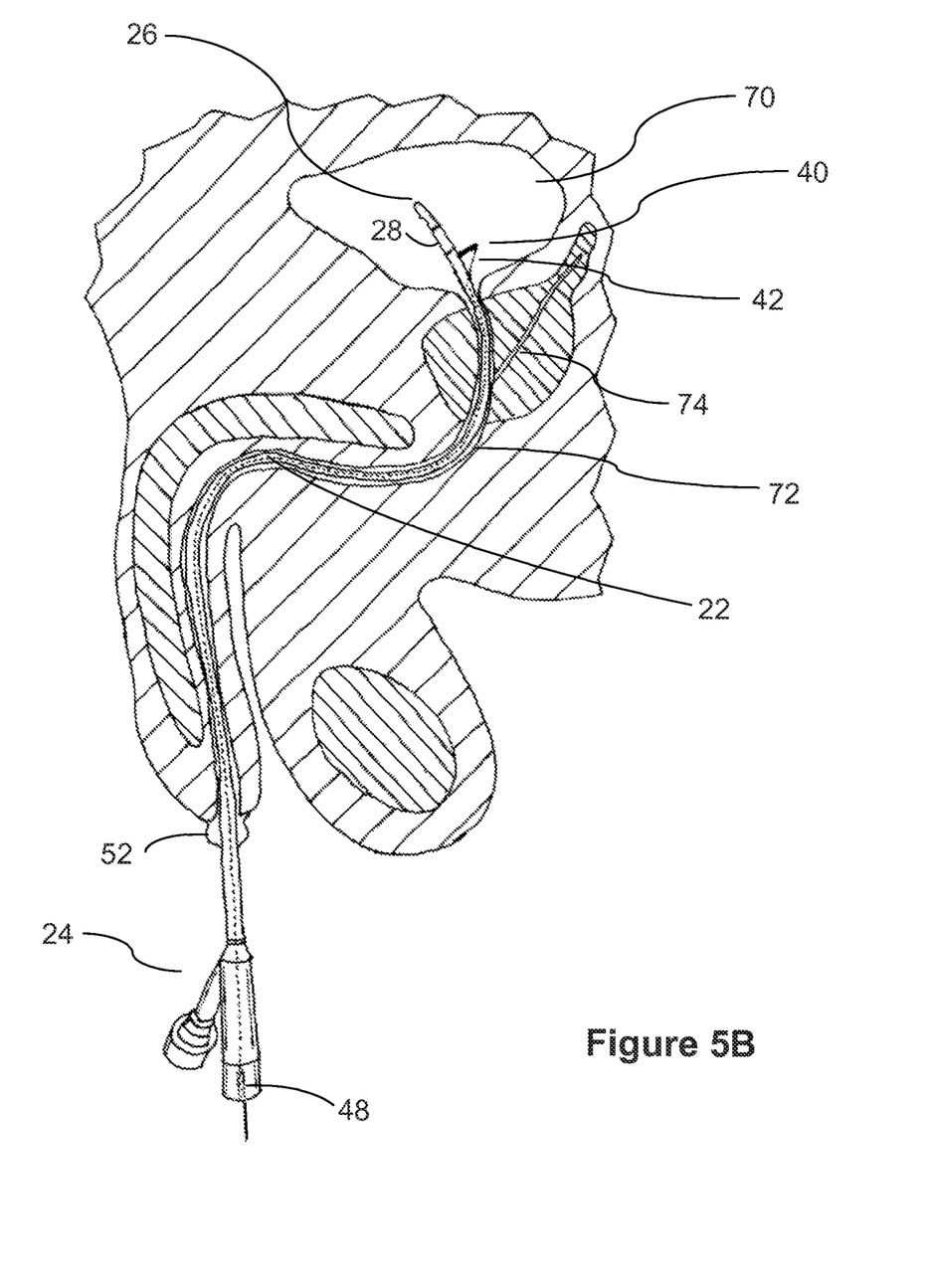
FIG. 5B is a side view of the urinary catheter of FIG. 5A after it has been inserted into the urinary bladder in accordance with one embodiment.

FIGS. 5A and 5B are side views showing placement of a catheter provided herein (e.g., catheter 20) relative to the urinary tract of a male patient. Catheter 20 can also be used for a female patient. As shown in FIG. 5A, an introducer 52 can be used to insert distal end 26 of catheter 20 into the meatus opening in the patient into the urinary canal 74 towards bladder 70. As shown, distal end 26 is within the urinary canal 74. The wall of the urinary canal presses against flexible safety element 40 thereby causing safety element 40 to fold against the longitudinal axis of catheter body 22. Indicator 48 on communication structure 42 is visible outside the body near proximal end 24 of catheter 20, indicating that retention balloon 28 should not be inflated. If catheter 20 is pushed into a false lumen 74 instead of bladder 70, indicator 48 will still be visible since the force of the lumen wall will keep safety element 40 in the folded configuration. False lumen 74 may be shorter and/or wider than the one depicted in FIGS. 5A and 5B. In some cases, false lumen 74 is nearly the exact dimensions of catheter 20 since it is created when catheter 20 is being advanced towards the bladder.

FIG. 5B shows distal end 26 of catheter 20 inside bladder 70. Flexible catheter body 22 extends from bladder 70 through the meatus opening in the patient. Openings 38 on distal end 26 of catheter 20 transfer urine from the patient's bladder 70 to the urine storage bag 68 (not shown). Safety element 40 can be in an extended position, perpendicular to the longitudinal axis of catheter body 22. In the extended position, safety element can pull communication structure 42 distally, causing indicator 48 to no longer be visible at proximal end 26. When indicator 48 on communication structure 42 is no longer visible at proximal end 26, this signals that retention balloon 28 is fully inside bladder 70 and pump 62 (not shown) can be used to inflate retention balloon 28.

Figure 6:
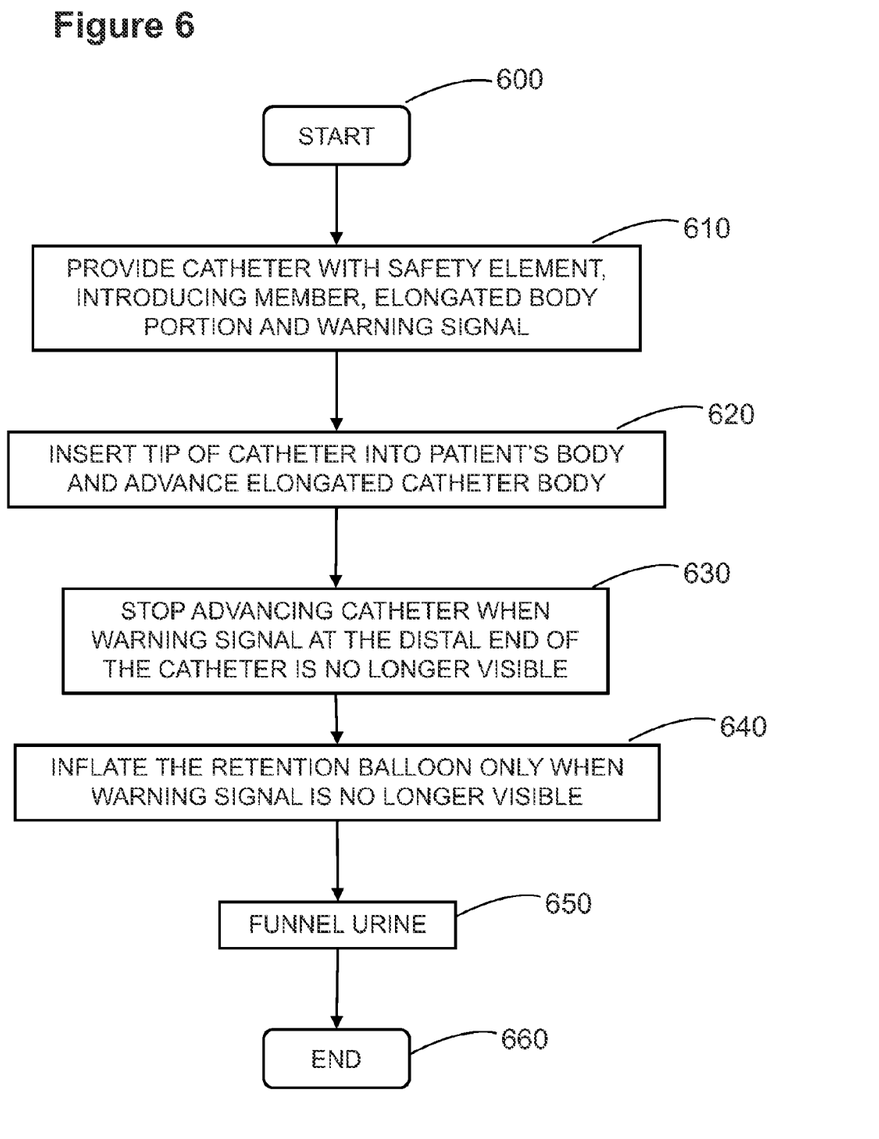
FIG. 6 is a process of using a catheter with a safety mechanism to prevent premature inflation of the retention balloon in accordance with one embodiment.

FIG. 6 is a process of using a catheter provided herein (e.g., catheter 20). It will be appreciated by the skilled practitioner that the illustrated process can be modified in a variety of ways. For example, appropriate sterilization techniques and application of lubrications can be performed.

As shown in FIG. 6, a process can start at step 600. At step 610, a catheter is provided comprising an introducing member, elongated flexible body portion, and a safety mechanism. A urine storage bag and pump may be connected to a catheter funnel at this time if the communication structure of a safety mechanism does not pass through the inflation lumen or the drainage lumen. At step 620, the catheter can be inserted into the patient and advanced along the urinary canal. While the catheter is being advanced, the indicator at the distal end of the catheter is visually monitored. At step 630, advancing the catheter is stopped when the indicator is no longer visible or it has shifted distally from an originally position. At this point, the presence of the distal end of the catheter within the bladder can be confirmed by gently pulling on the communication structure and watching the indicator appear and disappear. If the safety mechanism is removable, the communication structure can be pulled until the safety element breaks free from the catheter body. Subsequently, at step 640, the retention balloon can be inflated, and the patient's urine is funneled through the catheter and into a urine storage bag at step 650. The process can end at step 660.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A catheter comprising:
(a) a body defining a lumen and having a proximal portion and a distal portion,
(b) a retention balloon near an end of said distal portion,
(c) a safety element on said body located proximal to said retention balloon, wherein said catheter is configured such that said safety element changes position when said retention balloon is inside a body cavity, and
(d) a communication structure connected to said safety element, wherein said communication structure is a suture that extends from a tip of said safety element to said proximal portion.

2. The catheter of claim 1, wherein said safety element comprises a flap located proximal to said retention balloon.

3. The catheter of claim 2, wherein said flap is folded against said body while said catheter is inserted, and wherein said flap is extended away from said body when said retention balloon is inside said body cavity.

4. The catheter of claim 2, wherein said flap is latex.

5. The catheter of claim 1, wherein said catheter is a urinary catheter.

6. The catheter of claim 1, wherein said catheter is a Foley catheter.

7. The catheter of claim 1, wherein said body cavity is a urinary bladder.

8. A catheter comprising:
(a) a body defining a lumen and having a proximal portion and a distal portion,
(b) a retention balloon near an end of said distal portion,
(c) a safety element on said body located proximal to said retention balloon, wherein said catheter is configured such that said safety element changes position when said retention balloon is inside a body cavity, and
(d) a communication structure connected to said safety element, wherein said communication structure comprises an indicator that signals when said safety element is in an extended or non-extended position.

9. The catheter of claim 8, wherein said safety element comprises a flap located proximal to said retention balloon.

10. The catheter of claim 9, wherein said flap is folded against said body while said catheter is inserted, and wherein said flap is extended away from said body when said retention balloon is inside said body cavity.

11. The catheter of claim 9, wherein said flap is latex.

12. The catheter of claim 8, wherein said catheter comprises a communication structure connected to said safety element.

13. The catheter of claim 8, wherein said catheter is a urinary catheter.

14. The catheter of claim 8, wherein said catheter is a Foley catheter.

15. The catheter of claim 8, wherein said body cavity is a urinary bladder.

16. A method for using a catheter comprising:
    (a) inserting a catheter into a patient, wherein said catheter comprises (i) a body defining a lumen and having a proximal portion and a distal portion, (ii) a retention balloon near an end of said distal portion, (iii) a safety element attached to said body and located proximal to said retention balloon, and (iv) a communication structure attached to said safety element and configured to signal the position of said safety element to a user when said safety element is within said patient, and
    (b) inflating said retention balloon after said safety element signals when said retention balloon is inside a body cavity, wherein said communication structure is a suture that extends from a tip of said safety element to said proximal portion.

17. The method of claim 16, wherein said safety element comprises a flap located proximal to said retention balloon.

18. The method of claim 17, wherein said flap is folded against said body while said catheter is inserted, and wherein said flap is extended away from said body when said retention balloon is inside said body cavity.

19. The method of claim 17, wherein said flap is latex.

20. The method of claim 16, wherein said catheter is a urinary catheter.

21. The method of claim 16, wherein said catheter is a Foley catheter.

22. The method of claim 16, wherein said body cavity is a urinary bladder.

23. The method of claim 16, wherein said user is a nurse or medical assistant.

24. A method for using a catheter comprising:
    (a) inserting a catheter into a patient, wherein said catheter comprises (i) a body defining a lumen and having a proximal portion and a distal portion, (ii) a retention balloon near an end of said distal portion, (iii) a safety element attached to said body and located proximal to said retention balloon, and (iv) a communication structure attached to said safety element and configured to signal the position of said safety element to a user when said safety element is within said patient, and
    (b) inflating said retention balloon after said safety element signals when said retention balloon is inside a body cavity, wherein said communication structure comprises an indicator that signals when said safety element is in an extended or non-extended position.

25. The method of claim 24, wherein said safety element comprises a flap located proximal to said retention balloon.

26. The method of claim 25, wherein said flap is folded against said body while said catheter is inserted, and wherein said flap is extended away from said body when said retention balloon is inside said body cavity.

27. The method of claim 25, wherein said flap is latex.

28. The method of claim 24, wherein said catheter is a urinary catheter.

29. The method of claim 24, wherein said catheter is a Foley catheter.

30. The method of claim 24, wherein said body cavity is a urinary bladder.

31. The method of claim 24, wherein said user is a nurse or medical assistant.

\* \* \* \* \*